(12) United States Patent
Gewiese

(10) Patent No.: US 7,167,001 B2
(45) Date of Patent: Jan. 23, 2007

(54) INSTALLATION FOR INVESTIGATING OBJECTS USING MAGNETIC RESONANCE

(75) Inventor: Bernd Gewiese, Straubenhardt (DE)

(73) Assignee: Bruker Biospin MRI GmbH, Ettlingen (DE)

(*) Notice: Subject to any disclaimer, the term of this patent is extended or adjusted under 35 U.S.C. 154(b) by 25 days.

(21) Appl. No.: 11/056,152

(22) Filed: Feb. 14, 2005

(65) Prior Publication Data
US 2005/0200360 A1    Sep. 15, 2005

(30) Foreign Application Priority Data
Feb. 20, 2004   (DE) .................... 10 2004 008 343

(51) Int. Cl.
*G01V 3/00* (2006.01)

(52) U.S. Cl. ...................... 324/318; 324/322
(58) Field of Classification Search ............... 324/318, 324/322, 319, 300; 600/410–422; 355/296
See application file for complete search history.

(56) References Cited

U.S. PATENT DOCUMENTS

| 5,623,241 A | * | 4/1997 | Minkoff ...................... 335/296 |
| 6,567,683 B1 | | 5/2003 | Knuettel |
| 7,003,344 B1 | * | 2/2006 | Bolas et al. ................ 600/410 |

* cited by examiner

*Primary Examiner*—Brij B. Shrivastav
(74) *Attorney, Agent, or Firm*—Paul Vincent

(57) ABSTRACT

An installation for the investigation of objects by means of magnetic resonance has a magnet system for the production of a homogenous magnetic field in an investigational volume and is characterized in that the magnet system is disposed in a magnet room and the investigational volume, in a first operational mode of the installation, is disposed in a safety room which is decoupled in a gas-tight fashion from the magnet room. The installation in accordance with the invention facilitates the investigation of contaminated objects by means of magnetic resonance, wherein the measurement apparatus is not contaminated and simultaneously allows for simple maintenance of the system external to the safety room as well as a simple positioning of the object under investigation.

20 Claims, 3 Drawing Sheets

INSTALLATION FOR INVESTIGATING OBJECTS USING MAGNETIC RESONANCE

This application claims Paris Convention priority of DE 10 2004 008 343.6 filed Feb. 20, 2004 the complete disclosure of which is hereby incorporated by reference.

BACKGROUND OF THE INVENTION

The invention concerns an installation for the investigation of objects using magnetic resonance, having a magnet system for producing a homogenous magnetic field in an investigational volume.

An installation of this kind is by way of example described in U.S. Pat. No. 6,567,683B1.

Research activities for the development of therapies and vaccines in conjunction with highly infectious viruses which can be transferred by aerosols, as well as research with genetic manipulated and biological, chemical or radioactively contaminated objects as well as poisonous chemical weapons (ABC weapons) all require a high level of safety. Objects of this kind must therefore be investigated in a safe room from which no gas exchange occurs with the environment. For research on such objects, among other things, measurements using magnetic resonance are of interest. Since apparatuses which are disposed within the safety room can also become contaminated, these devices can no longer be used to investigate non-contaminated objects. Therefore, in order to investigate contaminated and non-contaminated objects, separate apparatuses are generally required. The acquisition of a plurality of apparatuses for measuring magnetic resonance is, however, extremely expensive.

An additional problem concerns the maintenance of contaminated spaces in which the apparatuses are disposed since the maintenance personnel have a presence in the safety room during the maintenance procedure, for example when filling liquid helium for superconducting coils. This requires additional safety measures to protect the personnel (safety suits, disposal of the safety clothing, health monitoring of the personnel and the like) and is also associated with significant risks for the technical personnel, in particular since the risks associated with contamination are often underestimated on the part of the technical personnel. A large fraction of the maintenance work is therefore often carried out by scientifically educated personnel, leading to a unnecessary increase in maintenance costs.

It is therefore desirable for measurements of contaminated objects, to minimize both the costs for acquisition of a corresponding measuring apparatus as well as other costs concerning maintenance as well as to minimize the risk for personnel.

In particular, for example, investigations of gene manipulated animals require extremely high safety precautions to prevent escape of the animal. The animals are generally investigated in an anaesthetized condition and should the animal regain consciousness, one must assure that the gene manipulated animal does not escape.

U.S. Pat. No. 6,657,683B1 discloses a device for carrying out nuclear resonance measurements on a body part of a large animal. The apparatus includes a housing adapted to the shape of the large animal. This housing has a protrusion for acceptance of a body part which can be introduced into the magnet configuration. The radio frequency device can be introduced onto this protrusion. Although this facilitates the investigation of animals and escape of the animal, even without sedation, is prevented, an investigation of highly contaminated objects is not possible.

In contrast thereto, it is the purpose of the present invention to propose an installation for investigation of contaminated objects using magnetic resonance with which the measuring apparatus does not become contaminated, wherein a simple maintenance of the system without the danger of contaminating the maintenance personnel as well as a simple positioning of the investigational object are facilitated.

SUMMARY OF THE INVENTION

This purpose is achieved in a surprisingly simple but effective manner by means of an installation of the above mentioned kind with which the magnet system is in a magnet room and the investigational volume is located, in a first operational state of the installation, in a safety room which is decoupled in a gas-tight fashion from the magnet room.

The installation in accordance with the invention provides a topological separation between the investigational volume and the magnet configuration without encroaching upon the measurement. The technical activities and maintenance of the magnet system can thereby be carried out by technicians without having to enter into the safety region. In the event of emergency, the entire magnet system can be removed without damaging the jacket of the safety region and can be exchanged for another magnet system. An unnecessary danger to the technical personnel is avoided by the installation in accordance with the invention. Moreover, the installation achieves improved safety with regard to the objects to be investigated relative to the external environment, since the risk of escape of contamination and/or of the object itself is reduced in that the safety room must only be entered for preparation and possible positioning of the measuring object.

The advantages of the invention are particularly effective in an embodiment with which the contaminated object to be investigated and the safety room are configured in such a way that no contamination can escape from the safety room. This facilitates, for the first time, the investigation of highly contaminated objects using magnetic resonance without having the measuring apparatus and/or the environment be contaminated.

Underpressure is preferentially present in the safety room relative to the outer atmosphere. This guarantees that, in the event of a possible leakage in the installation, there is no gas transfer from the outside into the safety room and vice versa.

The safety room is advantageously accessible through at least one lock. Due to the generally smaller volume of the lock, poisonous gases or aerosols can be pumped off from the lock room relatively quickly. This is particularly advantageous for exchanging and disposing of contaminated protective clothing.

In a particularly preferred embodiment of the invention, the safety room is provided with an air-filtering system or is connected thereto. Air which is infected with poisonous substance or viruses can be pumped out of the room through this air filtering system and can be filtered and cleaned. With the assistance of a controlled air exchange, entry into the safety room, for example to remove objects, is made significantly more easier.

In a preferred embodiment of the invention, the object to be investigated is disposed in a closed container during the investigation. Small objects can be easily handled in this manner.

The closed container is preferentially disposed in the safety room during the measurement. In this fashion, escape of e.g. an animal to be investigated from the laboratory is rendered more difficult.

In a special improvement of this embodiment, the container constitutes the safety room. The container can be completely removed from the magnet system following the measurement.

In a particularly preferred embodiment of the installation in accordance with the invention, the magnet system, in a first operational state of the installation, substantially surrounds the investigational volume and the safety room, in this first operational state, projects into the magnet system while exhibiting a bulge. With the assistance of the bulge, the object in the safety room can be easily positioned in the homogenous field region of the magnet system and is nevertheless separated from that magnet system in a gas-tight manner.

In a particular advantageous embodiment, the safety room bulge is flexible and moveable, in particular, comprises a bellows, a telescoping system, or a non-tearing foil. The bulge can therefore be adapted in an optimal fashion to the respective application by either being introduced into the investigational volume or, if required, removed from the investigational volume.

It is particularly advantageous for handling purposes when the magnet system can be moved relative to the safety room or relative to portions of the safety room and/or vice versa.

The magnet system or parts of the side walls surrounding the magnet system can preferentially be moved in such a fashion that the magnet system is freely accessible from all sides, at least in a non-operational state. In this manner, the installation can be subjected to maintenance without having to enter the safety region.

It is moreover advantageous when the investigational volume for magnetic resonance measurements of non-contaminated objects, in a second operational state, is disposed in the magnet room. This can, in particular, be effected by removal of portions of the safety room, in particular the above described bulge. The investigational volume disposed within the magnet system is then located in the magnet room and can be utilized for investigation of non-contaminated objects. The installation is thereby multifunctional and, moreover, can be operated continuously.

In a further embodiment of the invention, the investigational volume is surrounded by an RF (radio frequency) receiving and/or irradiating antenna which is disposed in the magnet room and the wall between the magnet room and the safety room is transparent to the RF radiation in the region of the RF antenna. The RF radiation can thereby be irradiated from the magnet room into the investigational volume and the irradiation emitted from the object can be detected in the magnet room. A wall which is transparent to RF radiation and disposed between the magnet room and the safety room is also necessary in MRI measurements due to the normally utilized pulsed gradients. RF measurement and/or irradiation antennas can accordingly be disposed in the magnet room and, with the assistance of the configuration in accordance with the invention, are not disturbed by contamination in the safety room.

In a preferred improvement of this embodiment, at least a part of the wall between the magnet room and the safety room is made from polytetrofluoroethylene (Teflon®). Due to its di-electrical properties this material is well suited for the stated application. In principle, any arbitrary di-electric can be utilized as long as it does not emit a magnetic resonance signal (usually a proton signal) when irradiated with RF.

In a further embodiment of the installation in accordance with the invention, the investigational volume is surrounded by an RF measurement and/or irradiating antenna which is disposed in the safety room. In this manner, the RF antenna can be disposed particularly close to the object under investigation or in the object (for example in a body cavity).

The investigational volume as well as the RF system are advantageously disposed in a Faraday cage so that the region in which the RF signal is irradiated and emitted is shielded from external interference. It is, however, also conceivable for the entire safety room and even also the magnet room to be disposed within a Faraday cage.

In a further preferred configuration of the installation, gas-tight electrical feed-throughs are provided between the safety room and the magnet room. This facilitates, e.g. signal passage from the RF antenna disposed in the safety room into the magnet room such that the measuring data can be recorded. Clearly, such feed-throughs can also be provided in other rooms.

In a particular preferred embodiment of the invention, wireless, in particular optical signal transfer means, e.g. windows or fiberglass cables, are provided to transport signals between the safety room and the magnet room. In this manner, the number of gas-tight electrical feed-throughs between the safety room and the magnet room is reduced.

Moreover, it can also be advantageous if the safety room is provided with disposable RF antennas which can be discarded following use so that the transfer of contamination to another object via these RF antennas can be avoided.

Further advantages of the invention can be derived from the description and the drawings. The above mentioned features as well as those discussed below can be utilized individually or collectively in arbitrary combination. The embodiments shown and described are not to be considered exhaustive enumeration rather have exemplary character for illustrating the invention.

DESCRIPTION OF THE PREFERRED EMBODIMENT

Figure 1:
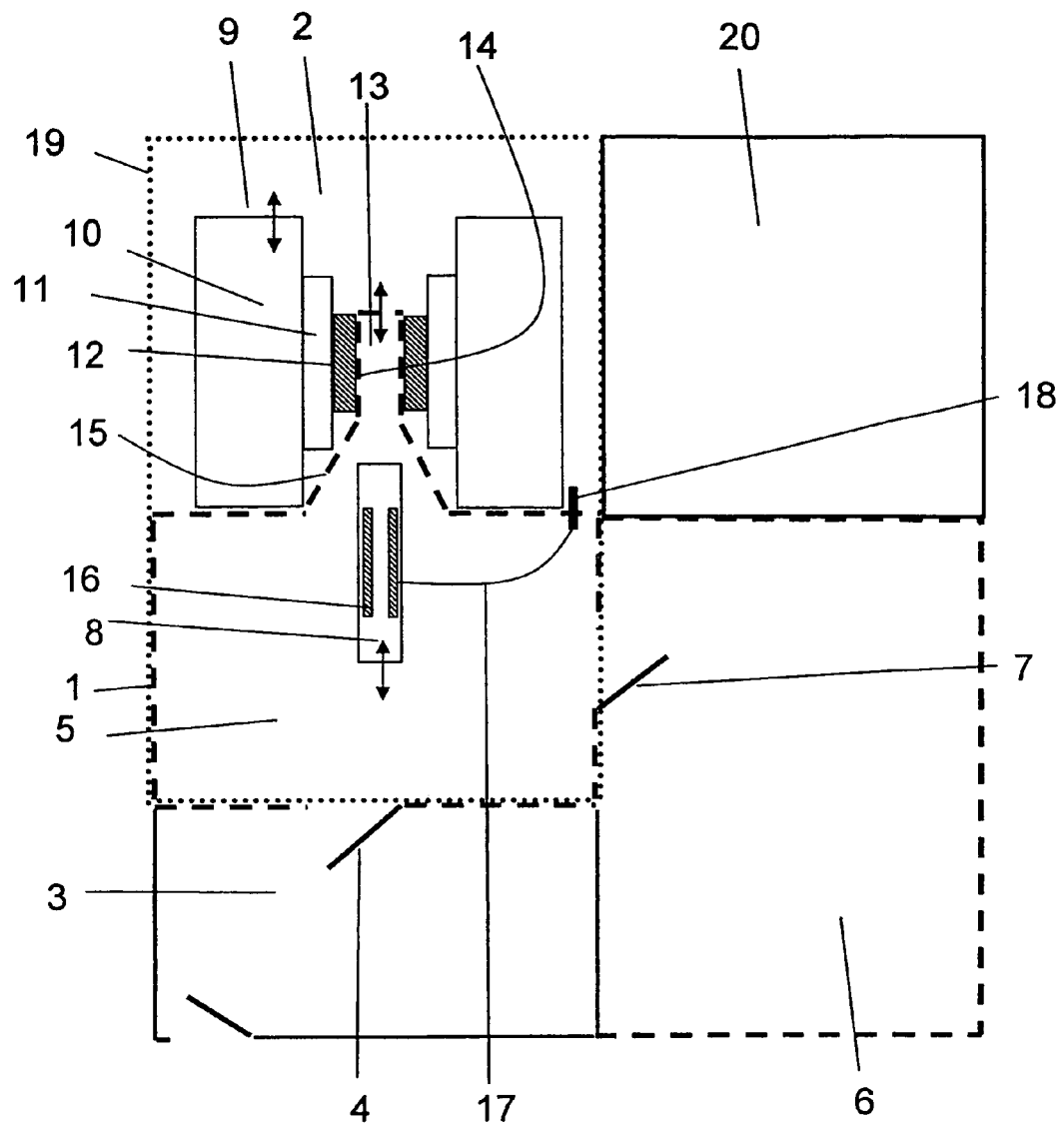
FIG. 1 shows an installation in accordance with the invention for the investigation of objects using magnetic resonance in a first operational state and having a Faraday cage outside of the magnet configuration.

FIG. 1 shows an installation for the investigation of objects using magnetic resonance including a safety room 1 and a magnet room 2. The safety room 1 can be entered through a lock 3 which is separated from the neighboring safety room 1 by means of a gas-tight and pressure resistant door 4. The safety room 1 is separated into a measuring region 5 and an object preparation region 6 which are likewise separated from each other by means of a RF sealed door 7. All measurement and anesthesia devices that are necessary for the experiment are located in the safety room 1. The measuring object can be prepared for the measurement using a transportable object pallet 8.

A magnet system 9 is disposed in the magnet room 2 which includes a magnet 10, gradient coils 11 and a resonator 12. The investigational volume 13 in which the measurements of magnetic resonance are carried out, is located within the resonator 12 and is surrounded by the magnet system 9.

The safety room has a region exhibiting a bulge 14 which can project, in a first operational state, into the investigational volume 13 so that the investigational volume 13 actually lies in the safety room. By means of the transportable object pallet 8, a prepared object can be transferred into the investigational volume 13 without having to leave the safety room 1. In this manner, the magnet system 19 is not contaminated during the measurement. The measuring console for the apparatus is preferentially disposed in another additional room 20 which is not subject to the safety requirements of the safety room and is thereby freely accessible.

During magnetic resonance measurements, radio frequency pulses are irradiated from and received by an RF antenna. The transmission and receiving antenna can be disposed in the magnet room 2 in such a fashion that transmission of the irradiated or of the RF radiation emitted from the object must pass through the wall 15 disposed between the magnet room and the safety room which has a region transparent to the RF radiation. In order to carry out the magnetic resonance measurements, a portion of the wall 15 must accordingly be configured to be RF permeable, that portion being disposed between the magnet room 2 and the safety room 1 and, in particular, at least the region which is located in the investigational volume. This can be effected by means of a suitable material such as e.g. Teflon® or Plexiglas.

For some investigations, it is necessary to introduce the RF receiving antennas very close or actually in contact with the object under investigation. Towards this end, the invention provides that a resonator 12 cannot only be provided in the magnet room 2 but for such applications additional RF measurement and/or irradiation antennas 16 can be provided in the safety room. Such coils could also be throw-away coils which can be disposed of after the investigation of the object in order to avoid subsequent contamination of other investigated objects by the contaminated RF receiver coils. The measurement signals received from the RF measurement and/or irradiation antenna 16 are then transferred from the safety room 1 into the magnet room 2 by means of electrical leads 17 which pass through gas-tight feedthroughs 18 or by means of wireless, in particular, optical signal transfer means.

Figure 2:
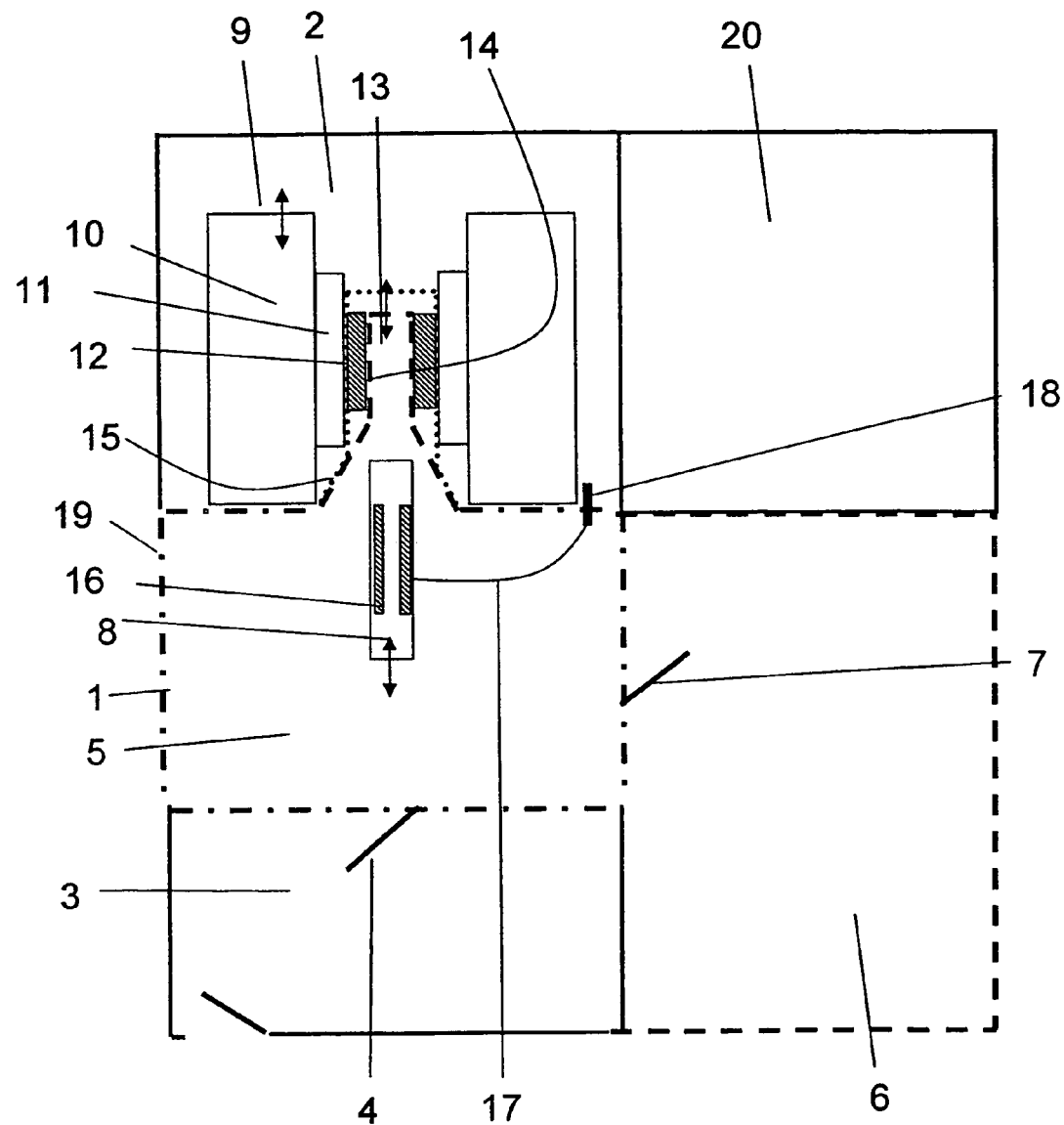
FIG. 2 shows an installation in accordance with the invention for the investigation of objects using magnetic resonance in a first operational state having a Faraday cage disposed within the magnet configuration.

FIG. 1 shows the safety room 1 (dashed lines) and the magnet room 2 both of which are surrounded by a Faraday cage 19 for RF shielding. It is, however, not absolutely necessary that the Faraday cage 19 surrounds the magnet system 9. As shown in FIG. 2 the Faraday cage 19 can also be disposed within the magnet system 9 so that the Faraday cage 19 (dotted lines) substantially includes the part of the bulge 14 projected into the investigational volume 13, the resonator 12 and the measurement region 16 of the safety room 1.

Figure 3:
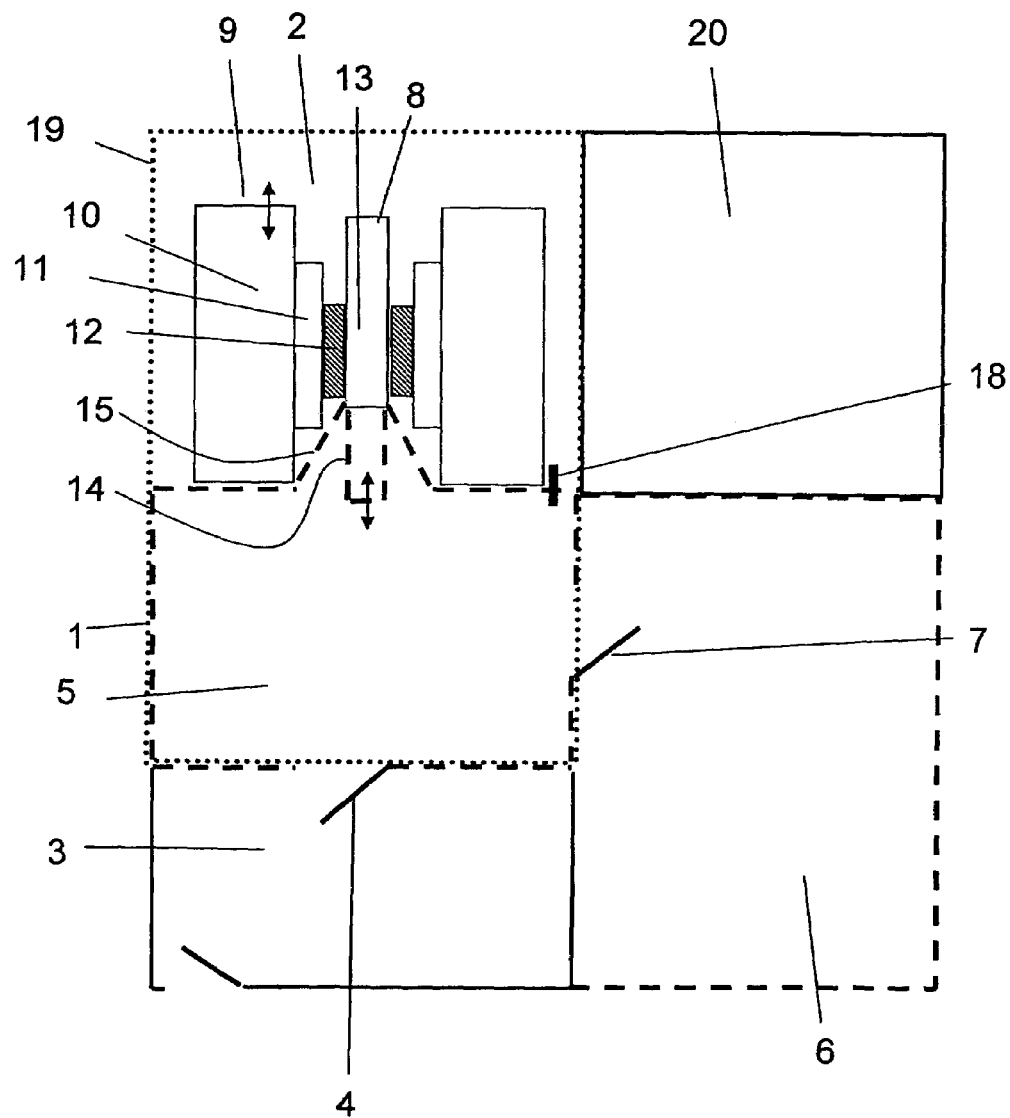
FIG. 3 shows an installation in accordance with the invention for the investigation of objects using magnetic resonance in a second operational state.

The bulge 14 is gas-tight and preferentially flexible. If necessary, the bulge 14 can be removed from the investigational volume 13 such that the installation can be operated in a second operational state. FIG. 3 shows a configuration in accordance with the invention in a corresponding second operational state with which the bulge 14 is folded over and the investigational region 13 is then disposed in the magnet region 2. This can, e.g. be effected through the utilization of flexible materials, e.g. a bellow system made from strong foil. However, it is also conceivable to construct a rigid bulge 14 through a corresponding mechanical configuration, e.g. in the form of a telescoping system. In this fashion the bulge 14 can be advanced or retracted. It is also advantageous when the bulge 14 is fashioned from a transparent material so that one can view the investigational volume 13 located in the bulge 14 from the magnet room 2.

By means of removal of the bulge 14 out of the investigational region 13 the magnet system 9 can be used for "conventional" measurement of non-contaminated objects in the magnet room. In this manner, the magnet system 9 can be optimally utilized to avoid downtime and non-use of the apparatus. Moreover, the magnet system 9 itself can be moved to thereby retract the bulge 14 from the investigational volume 13 and, following displacement, the magnet system 9 is freely accessible from all sides. This is particularly advantageous for maintenance of the magnet system 9 which, in accordance with the invention, can take place without entering the safety room 1.

The safety room must not necessarily be a stationary room. A moveable "safety container" is also conceivable which has the requirements of the safety room and is suitable for use in an installation in accordance with the invention as a result of which further flexibility for the installation and better capsuling of the contaminated objects is facilitated.

The installation in accordance with the invention is not only limited to applications within the context of magnetic resonance imaging (MRI) but is also applicable for other measurements, e.g. ISR or NMR spectroscopy, in particular for the investigation of ABC weapons. Towards this end, one may use a magnet with a vertical bore which is disposed one floor below the safety room. The safety room 1 has a bulge 14 in the floor which penetrates into the resonator of the vertical magnet system. In general, the construction of the installation in accordance with the invention is applicable for all kinds of contact free analytic procedures, in particular for those with which the measurement apparatus surrounds the investigational volume (e.g. CT). This, however, does not preclude use of the installation in accordance with the invention with open systems.

In its totality, a configuration for measurement of magnetic resonances is suitable for the investigation of highly contaminated objects which have an associated risk for human health and/or to the environment, wherein the installation in accordance with the invention permits simple and low risk maintenance. Maintenance personnel are therefore not subject to unnecessary dangers so that maintenance on the apparatus can be carried out by technical personnel. Moreover, the installation in accordance with the invention facilitates optimal use of the apparatus.

I claim:

1. An installation for the investigation of an object by means of magnetic resonance, the installation comprising:

a magnet system for production of a homogenous magnet field in an investigational volume;

a magnet room in which said magnet system is disposed; and a safety room, said safety room being decoupled from the magnet room in a gas-tight fashion, wherein the investigational volume is disposed in said safety room in a first operational state of the installation.

2. The installation of claim 1, wherein the object to be investigated is contaminated and said safety room is configured in such a manner that no contamination can escape from said safety room.

3. The installation of claim 1, wherein said safety room has an underpressure relative to an outer atmosphere.

4. The installation of claim 1, wherein said safety room is accessible through at least one lock.

5. The installation of claim 1, wherein said safety room is configured with an air-filtering system or is connected to such a system.

6. The installation of claim 1, wherein the object to be investigated is disposed in a closed container during the investigation.

7. The installation of claim 6, wherein said closed container is disposed in said safety room during the investigation.

8. The installation of claim 6, wherein said closed container constitutes said safety room.

9. The installation of claim 1, wherein, in said first operational state of the installation, said magnet system substantially surrounds the investigational volume and said safety room protrudes into said magnet system with a bulge.

10. The installation of claim 9, wherein said bulge is flexible, moveable, has a bellows, has a telescoping system, or has a non-tearing foil.

11. The installation of claim 1, wherein said magnet system and at least parts of said safety room can be moved relative to each other.

12. The installation of claim 11, wherein at least parts of said magnet system have surrounding side walls which can be moved in such a fashion that said magnet system is accessible from all sides, at least in a non-operational state thereof.

13. The installation of claim 11, wherein for the investigation of objects which are not contaminated, the investigational volume is disposed in the magnet room in a second operational state.

14. The installation of claim 1, wherein the investigational volume is surrounded by a RF (radio frequency) measurement and/or irradiation antenna which is disposed in said magnet room and a wall between said magnet room and said safety room is transparent to RF radiation in a vicinity of said RF antenna.

15. The installation of claim 14, wherein least portions of said wall between said magnet room and said safety room are made from polytetrafluoroethylene (Teflon®).

16. The installation of claim 1, wherein the investigational volume is surrounded by an RF (radio frequency) measurement and/or irradiation antenna disposed in said safety room.

17. The installation of claim 1, further comprising a Faraday cage within which at least the investigational volume as well as an RF system is disposed.

18. The installation of claim 1, further comprising gastight electrical feed-throughs disposed between said safety room and said magnet room.

19. The installation of claim 1, further comprising wireless or optical, signal transfer means for transfer of signals between said safety room and said magnet room.

20. The installation of claim 1, wherein throw-away RF antennas are disposed in said safety room for disposal following use thereof.

* * * * *